United States Patent [19]
Gelb

[11] Patent Number: 5,208,845
[45] Date of Patent: May 4, 1993

[54] RADIOGRAPHIC DEPTH GAUGE

[76] Inventor: David A. Gelb, 47 Norwood, West Hartford, Conn. 06117

[21] Appl. No.: 830,604

[22] Filed: Feb. 4, 1992

[51] Int. Cl.⁵ ............................................... A61B 6/14
[52] U.S. Cl. .................................. 378/163; 378/170; 378/205
[58] Field of Search ................. 378/163, 170, 204, 205

[56] References Cited

U.S. PATENT DOCUMENTS

| | | | |
|---|---|---|---|
| 4,005,527 | 2/1977 | Wilson et al. | 378/163 |
| 4,279,252 | 7/1981 | Martin | 378/163 |

Primary Examiner—David P. Porta
Assistant Examiner—Don Wong
Attorney, Agent, or Firm—Helfgott & Karas

[57] ABSTRACT

A radiographic depth gauge for precisely positioning dental implants in a jaw bone. The gauge is formed of a material which will show on an x-ray and is an elongated member with distance markings. The gauge is placed in a bore drilled in a jaw bone and an x-ray is taken in a standardized manner to show true dimensions of the gauge on the film relative to surrounding anatomical structures. The gauge both shows the depth and angulation of the bore relative to other bores and existing dentition.

15 Claims, 2 Drawing Sheets

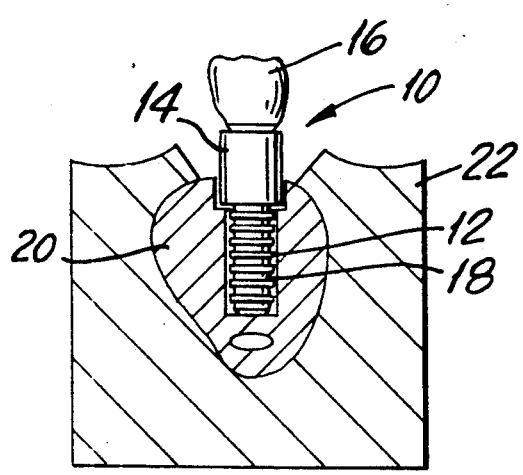
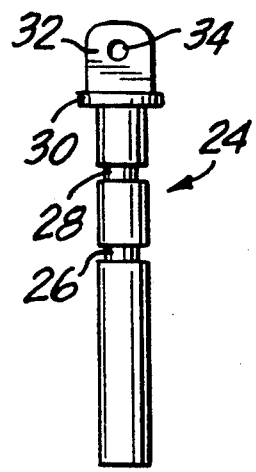
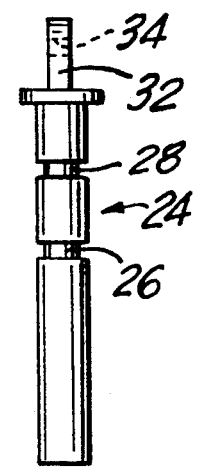
FIG.1  FIG.3  FIG.4
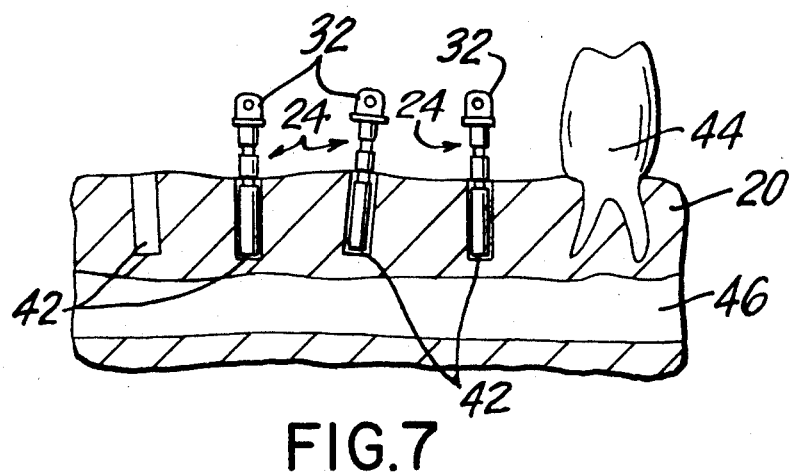
FIG.7

RADIOGRAPHIC DEPTH GAUGE

BACKGROUND OF THE INVENTION

This invention relates to a radiographic depth gauge and a method of placing implants, and more particularly to a depth gauge and method which permits the precision placement of implants to their maximum depth in a jaw bone to assure a maximum strength supporting structure for one or more dental restorations. In addition, this invention relates to a depth gauge which also permits accurate parallel alignment of multiple implants so that a high aesthetic level is achieved with the look of natural dentition when the dental restorations are in place.

In order to restore dentition where there are one or more teeth missing, a modern technique is used which is called implant dentistry. Implant dentistry relies on the bonding of the implant to the jaw bone which is to receive one or more implants. A bore is formed in the bone by drilling and a part of an implant called a fixture is secured in the bone. The gums are then sutured and for a period of months the bone adheres to the fixture through osseointegration. After the fixture is secure in the bone, the gums are surgically opened and a restoration supporting abutment is secured to the fixture. Ultimately, a restoration is secured to each abutment. For a complete discussion of implant dentistry, see "Tissue - Integration Prostheses" by Branemark/Zarb/Albrektsson published by Quintessence Publishing Co., Inc. For purposes of describing the invention, the Bramemark implant will be described.

Currently, preoperative planning relies on radiographic procedures which lack the precision needed for highly accurate implant dentistry. Typically, a series of x-rays are taken in order to determine where and how to position implants in the jaw bone without damaging surrounding structures such as the nerves in the lower jaw bone and the sinuses adjacent the upper jaw bone. It is important that x-rays be produced by a standardized procedure so that x-rays taken at various times may be readily compared. In addition, the x-rays should produce accurate images which neither lengthen nor shorten the object being x-rayed, i.e. a tooth which is 8 mm above the top of the crest of the jaw bone should be 8 mm above on the x-ray. One well known method for achieving the foregoing is to use a Rinn Bite Block placement for holding the x-ray film and aligning the x-ray source perpendicular to the film. In addition to full mouth and smaller x-rays, some practitioners use CAT scans. CAT scans are both expensive and difficult to interpret. Accordingly, the conservative interpretation of CAT scans has led to implants being secured to less than the maximum depth available in the jaw bone, resulting in inadequate support for the restorations. The practitioner may also have stents fabricated to help in the visualization of where to place the implants.

The practitioner using his available information drills a hole to the selected depth, usually a little smaller than the final diameter of the implant and may insert a periodontal probe to measure the depth which is read visually with some room for error since the probes have handles which protrude from the mouth. Also, a guide may be placed in each hole and viewed to ascertain visually whether the holes are parallel to one another and oriented properly with respect to remaining teeth. Again this is a visual process and subject to error caused by among other things, the angle of looking into a patient's mouth.

While the foregoing x-rays, CAT scans, probes, stents and guides have been useful in permitting the practitioner to place implants fairly accurately, still further improvements in devices for assuring the accurate placement of implants would be beneficial. These improvements would be particularly beneficial if they both permit securely placing the implants in maximum depth bores and aligning the implants so that the restored dentition cosmetically is appealing.

SUMMARY OF THE INVENTION

Accordingly, it is an object of the present invention to provide an improved device for determining the accurate placement of dental implants.

A further object of the present invention is to provide a depth gauge for radiographically determining the placement of an implant.

Still a further object of the present invention is to provide a radiographic depth gauge with markings indicative of implant lengths, which markings are readable on an x-ray.

Another object of the present invention is to provide a gauge which may be placed in each of a number of bores to radiographically determine the angulation of the bores relative to one another and existing dentition.

A further object of the present invention is to provide a radiographic depth gauge which may be used with and will not interfere with standard x-ray techniques which show true dimensions on an x-ray.

Another objective is to provide a radiographic depth gauge with suitable markings corresponding with standard implant lengths.

Still another object of the present invention is to provide a readily retrievable depth gauge.

Another object of the present invention is to provide a method of placing an implant which permits placing the implant at maximum depth for improved retention.

A further object of the present invention is to provide a method of radiographically determining potential implant angulation to permit angulation correction.

A still further object of the present invention is to provide a method of taking x-rays of a gauge using standard x-ray techniques to provide true dimensions of the gauge on an x-ray.

Briefly, in accordance with the present invention there is provided a depth gauge which is made of a material which will show on an x-ray. The gauge is cylindrical and is of a diameter which is smaller than the diameter of an implant. The gauge has markings which in a preferred embodiment which correspond to the standard lengths of various implants.

Based on x-ray and other data, a pilot bore is drilled in a jaw bone. The gauge is inserted in the bore and an xra is taken to determine the angulation of the bore relative to existing dentition and the depth of the bore relative to anatomical restrictions. The x-ray is taken using a system which will show the gauge in its true dimensions relative to other structures. The appropriate depth and angulation is then chosen and, depending on the circumstances, either the pilot bore is extended or a final bore of a larger diameter is made for the implant. The gauge is provided with a retrieval end for removing the gauge. The height of the gauge above the crest of the ridge of the jaw bone and relative to existing dentition is chosen so that the patient can bite on an x-ray bite block without interference.

In another embodiment where there are multiple implants in a quadrant, a gauge is inserted in each bore. The x-ray will then show the angulation of the bores relative to one another and relative to existing dentition.

The aforementioned objects, features and advantages of the invention will, in part, be pointed out with particularity, and will, in part, become obvious from the following more detailed description of the invention taken, in part, with the drawings which form an integral part thereof.

BRIEF DESCRIPTION OF THE DRAWING

In the drawing:

FIG. 1 is a cross sectional view of a jaw bone showing a typical implant and tooth restoration;

FIG. 3 is a side view of a depth gauge in accordance with the present invention;

FIG. 4 is a side view of the depth gauge shown in FIG. 3 rotated ninety degrees;

FIG. 7 is a side view of a jaw bone sectioned along its length showing a multiplicity of bores in a quadrant with depth gauges in several of the bores.

In the various figures of the drawings like reference characters designate like parts.

DETAILED DESCRIPTION OF THE PREFERRED EMBODIMENT

Figure 2:
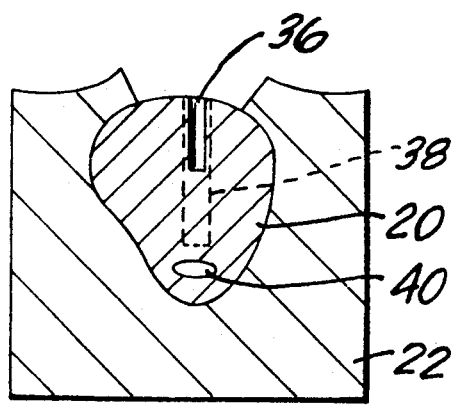
FIG. 2 is a cross sectional view of a lower jaw bone showing a pilot bore relative to a nerve carrying canal.

Referring now to the drawings, in FIG. 1 there is shown an implant generally designated as 10. The implant comprises a threaded fixture 12 and an abutment 14 which is threaded into the fixture 12. A tooth restoration 16 is secured on the abutment. The implant described iS the Branemark implant and is one of several which are on the market.

Fixture 12 is seated in a bore 18 in a jaw bone 20. The jaw bone 20 selected for discussion purposes is a lower jaw bone, but the same principles apply to the upper jaw bone. The fixture 12 shown for discussion is slightly larger in diameter than the bore and is screwed into the bore and made of titanium. The fixture adheres to the jaw bone by a process called osseointegration which takes place over a period of months. Tissue 22 covering the jaw bone 20 has been cut open to expose the abutment 14. A detailed description of implant procedures is set forth in a text entitled "Tissue-Integrated Prostheses" by Bramemark/Zarb/Albrektsson.

In order to determine where best to place implants, generally full mouth and individual x-rays are taken. CAT scans are sometimes also taken to help determine placement of implants for maximum strength while avoiding damaging various surrounding anatomies, e.g. nerves, roots and sinuses. The use of the x-rays and CAT scans give good approximations of the position of the implants relative to anatomical limitations. Accurate placement to enable aesthetic restorations of maximum strength require a gauge which is part of the x-ray and shows positions relative to the anatomical limitations on the x-ray.

A side view of a radiographic depth gauge 24 is shown in FIG. 3. The gauge is an elongated member such as a cylinder and is made of a material which shows clearly on an x-ray, such as a metal such as stainless steel. The gauge is of a diameter which is less than the diameter of an implant to allow, as will be described, for corrections in placement. Gauge 24 has two reduced diameter sections 26, 28 and an increased diameter cap 30. The reduced diameter sections 26, 28 and cap 30 are used as distance markers measuring from the bottom of the gauge since the reduced diameter sections show on the x-rays. The markers may be any indication which is visible on an x-ray, e.g. a hole through a gauge of uniform diameter. The cap 30 is of a larger diameter than the remainder of the gauge and, as will be described, prevents the gauge from going too deeply into a bore. The markers are selected to correspond with a manufacturers implant lengths. Using the Branemark system the markers are put at 7, 10 and 13 millimeters or 15, 18 and 20 millimeters measuring from the bottom of a gauge.

Gauge 24 is provided with a protrusion 32 above the cap 30. The protrusion 32, which has a hole 34 therein, acts as an insertion and retrieval end and provides a surface for gripping the gauge for insertion and removal from a bore. A thread or floss (not shown) may be inserted through the hole 34 and held outside a patient's mouth to protect against a patient swallowing or aspirating the gauge. In addition, the thread or floss can be used to assist in removing the gauge. FIG. 4 shows the gauge rotated ninety degrees from the position shown in FIG. 3 to show the shape of protrusion 32.

Figure 5:
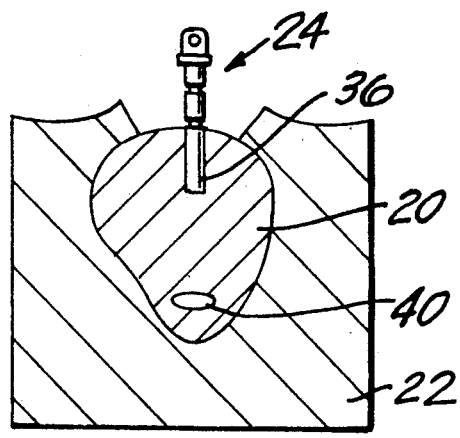
FIG. 5 is a view of the jaw bone shown in FIG. 2 with a depth gauge in the bore.

Referring to FIG. 2, a small pilot bore 36 is drilled into a jaw bone 18 which is the same diameter as the gauge. If a Bramemark fixture of 3.75 millimeters is to be used, a bore of 2 millimeters is sufficiently small to permit correction if the bore is not at the desired angle. For illustration, a final desired bore 38 is shown dotted which is drilled with a 3.3 millimeter drill at a different angle than the pilot bore 36. The 3.75 millimeter fixture will thread into the 3.3 millimeter bore without causing excess trauma. As can be seen the angle of the pilot bore can be changed with a larger diameter drill. Assuming the bore 36 is 7 millimeters in depth, a gauge having 7, 10 and 13 millimeter markings would be selected. As shown in FIG. 5, gauge 24 is inserted into the bore 36 and comes to rest at the 7 millimeter mark which is the first reduced diameter section 26.

Figure 8:
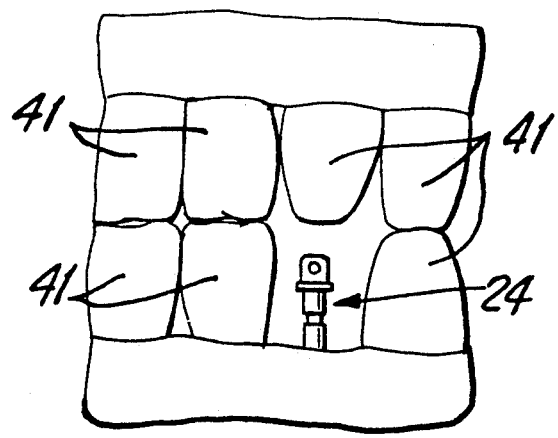
FIG. 8 is a view of a quadrant of teeth showing that the gauge does not interfere with biting.

In practice an x-ray would be taken which would show the exact position and angulation of the bore 36 which is identical to that of the gauge. The total length of the gauge and pilot bore are selected so that the gauge will not interfere with x-rays taken using a standard system such as the Rinn Bite Block system. A typical tooth averages between 6–8 millimeters in height above the crest of the jaw bone. Accordingly, the height of the protrusion is selected so that with a 7 millimeter bore, the distance to the top of the protrusion will be less than 8 millimeters, i.e. a protrusion of less than 2 millimeters in height. If the gauge interferes with an x-ray, the pilot bore is made deeper until there is no interference. As shown in FIG. 8, existing teeth 41 are able to close without interference from gauge 24.

The objective in taking an x-ray is to have the film parallel to the gauge and the x-rays perpendicular to the film and gauge. This is accomplished typically by using a long cone x-ray tube aligned with the external alignment ring of the Rinn Bite Block or equivalent system to get an anatomically correct picture. The distance between the bottom of the bore 36 and nerve canal 40 is measured on the film and the relationship to other bores and teeth is determined. The practitioner then can determine how much deeper to drill and the correct angulation. Using the x-ray as a guide, adjacent teeth can be marked with lines to assist in drilling at the selected angulation.

Figure 6:
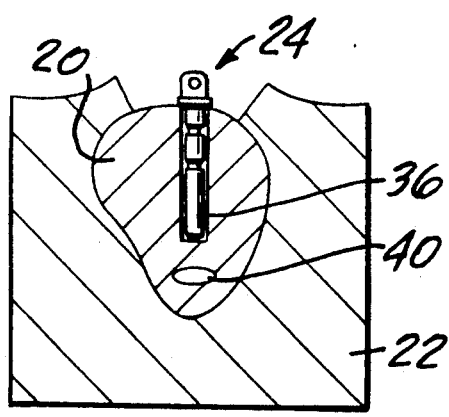
FIG. 6 is a view of the jaw bone shown in FIG. 5 with the bore drilled to a greater depth and the gauge inserted in the bore.

In FIG. 6, bore 36 has been drilled to a depth of 13 millimeters and consequently cap 30 at the 13 millimeter mark just touches and sits on the bone. As shown in FIG. 7 a quadrant of jaw bone 20 as viewed along its length is being prepared with multiple bores 42. Gauges 24 are inserted into the bores and an x-ray will show images of the gauges clearly depicting their angulation relative to one another and tooth 44 as well as proximity to canal 46. The practitioner can now make adjustments in angulation and drill accurately to a desired depth. When measurements are completed, the gauges are removed by gripping the protrusions 32 with a tweezer. Thread or floss inserted through holes 34 act to prevent swallowing or aspiration of the gauge.

The gauge permits precision placement of implants which improves their functionality and the aesthetic restorability of dentition. It also permits drilling in confidence in proximity to anatomical structures which are susceptible to damage.

There has been described a preferred embodiment of the invention and its use. However, it should be understood that various changes and modifications may be made which thereto without departing from the spirit and scope of the invention.

What is claimed is:

1. A radiographic depth gauge for determining the depth and angulation of a bore in a jaw bone for receiving dental implants, comprising:
   an elongated cylindrical member which is of a diameter substantially equal to the diameter of a drill used to form a pilot bore in a jaw bone, which bore is smaller than the diameter of the implant; and
   means which will show on an x-ray for indicating distances, which means is physically a part of the structure of the elongated member.

2. A depth gauge according to claim 1, which further comprises:
   a protrusion for inserting and removing the gauge from a bore.

3. A depth gauge according to claim 2, wherein:
   said protrusion has a hole for receiving a means for preventing the gauge from being swallowed.

4. A depth gauge according to claim 1, wherein:
   said distance indicating means comprises a reduced diameter portion of said elongated member.

5. A method of precisely positioning a dental implant in a jaw bone comprising the steps of:
   drilling a pilot hole of a selected diameter smaller than the diameter of an implant to a selected depth;
   placing a radiographic depth gauge of substantially the same diameter as the pilot hole into the pilot hole;
   positioning an x-ray film parallel to the depth gauge; and
   taking an x-ray with a parallel beam which is perpendicular to both the gauge and the film to determine on the x-ray the position of the pilot hole relative to anatomical structures as well as angulation.

6. A method of positioning an implant according to claim 5, comprising:
   drilling the pilot hole deeper than the selected depth;
   placing a radiographic depth gauge in the pilot hole; and
   taking an x-ray to further determine the position of the pilot hole.

7. A method of precisely positioning a dental implant in a jaw bone comprising the steps of:
   drilling a pilot hole of a selected diameter in a jaw bone;
   selecting a radiographic depth gauge of a length which will permit existing teeth to bite against one another when the gauge is in the pilot hole;
   placing the gauge in the pilot hole; and
   taking an x-ray of the gauge while the patient bites on a film holder.

8. A method of positioning an implant according to claim 7, comprising:
   positioning the x-ray source in an extension of the film holder which causes the x-ray to show true dimensions of the gauge on the film.

9. A method of precisely determining the position of a bore in a jaw bone relative to anatomical structures, comprising the steps of:
   placing a radiographic gauge in the bore;
   placing a film behind the gauge and anatomical structures;
   directing an x-ray beam perpendicular to the gauge and film so that true dimensions of the gauge are recorded on the film.

10. A method of making a radiographic depth gauge for the precision placement of dental implants comprising the steps of:
    fabricating an elongated member of a material which will be visible on an x-ray; and
    positioning markers on the elongated member which are physically a part of the structure of the elongated member and which are visible on an x-ray, which markers are at selected distances from a reference point on the elongated member.

11. A method of making a radiographic depth gauge according to claim 10, comprising the additional step of:
    making a protrusion at one end of the elongated member for gripping the gauge for insertion and removal from a bore.

12. A method of making a radiographic depth gauge according to claim 11, comprising the additional step of:
    making a hole in the protrusion for receiving a string or thread which may be secured outside a patient's mouth to prevent swallowing or aspiration of the gauge.

13. A method of making a radiographic depth gauge according to claim 10, wherein the selected distances correspond to the lengths of commercially available implants.

14. A method of making a radiographic depth gauge according to claim 13, comprising the additional step of:
    making the elongated member of a length which will most likely not interfere with a patient's ability to bite on an x-ray holder when the gauge is inserted into a bore in a jaw bone up to the shortest distance marker.

15. A method of making a radiographic depth gauge according to claim 14, comprising the additional step of:
    forming a protrusion at one end of the elongated member for gripping the gauge for insertion and renewal.

* * * * *